United States Patent [19]

Gifford, III et al.

[11] Patent Number: 4,669,469
[45] Date of Patent: Jun. 2, 1987

[54] SINGLE LUMEN ATHERECTOMY CATHETER DEVICE

[75] Inventors: Hanson S. Gifford, III, Palo Alto; John B. Simpson, Woodside, both of Calif.

[73] Assignee: Devices for Vascular Intervention, Redwood City, Calif.

[21] Appl. No.: 834,950

[22] Filed: Feb. 28, 1986

[51] Int. Cl.⁴ .............................................. A61B 17/32
[52] U.S. Cl. ................................................... 128/305
[58] Field of Search ................... 128/305, 751–755, 128/304, 303 R, 305.1; 604/22

[56] References Cited

U.S. PATENT DOCUMENTS

| | | | |
|---|---|---|---|
| 1,677,337 | 7/1928 | Grove | 128/305.1 |
| 3,173,414 | 3/1965 | Guillant | 128/752 |
| 3,561,429 | 2/1971 | Jewett | 128/305 X |
| 3,606,878 | 9/1971 | Kellogg | 128/753 |
| 3,844,272 | 10/1974 | Banko | 128/305 X |
| 4,513,745 | 4/1985 | Amoils | 128/305 |

FOREIGN PATENT DOCUMENTS

| | | | |
|---|---|---|---|
| 2804015 | 8/1979 | Fed. Rep. of Germany | 128/305 |
| 938977 | 7/1982 | U.S.S.R. | 128/305 |

*Primary Examiner*—Michael H. Thaler
*Attorney, Agent, or Firm*—Flehr, Hohbach, Test, Albritton & Herbert

[57] ABSTRACT

Atherectomy device for removing material from an atheroma in the vascular system. A cutter is mounted in a cylindrical housing having a cutout on one side thereof at the distal end of a catheter. The catheter has a single luminal opening, and a flexible drive cable for operating the cutter passes through this opening. An inflatable balloon is positioned outside the housing opposite the cutout, and a medium for inflating the balloon is introduced through the luminal opening of the catheter.

7 Claims, 2 Drawing Figures

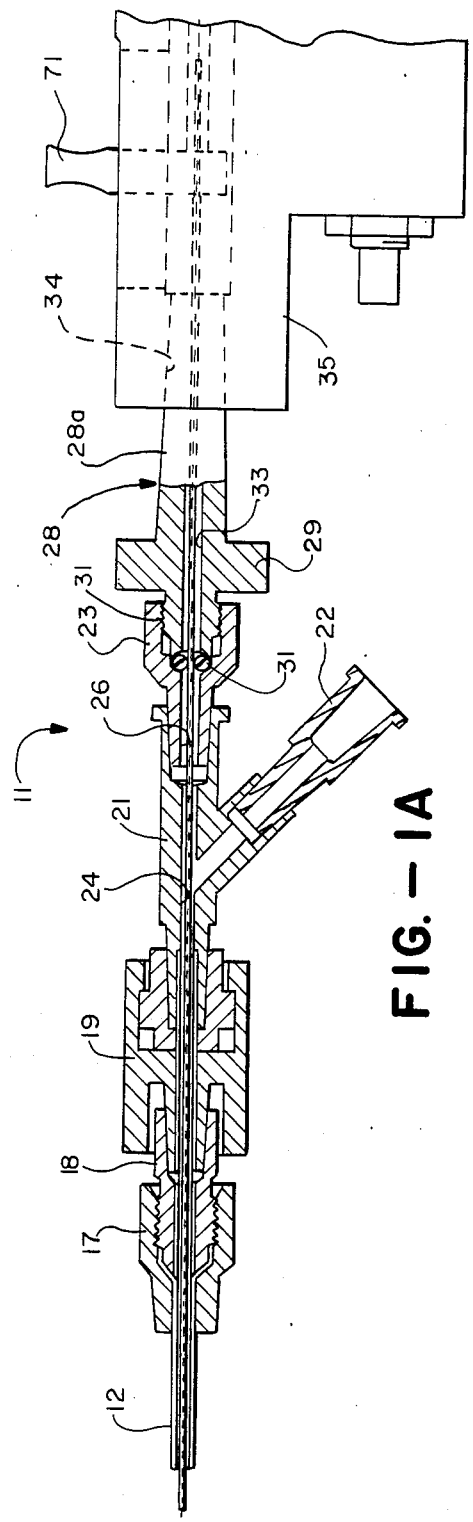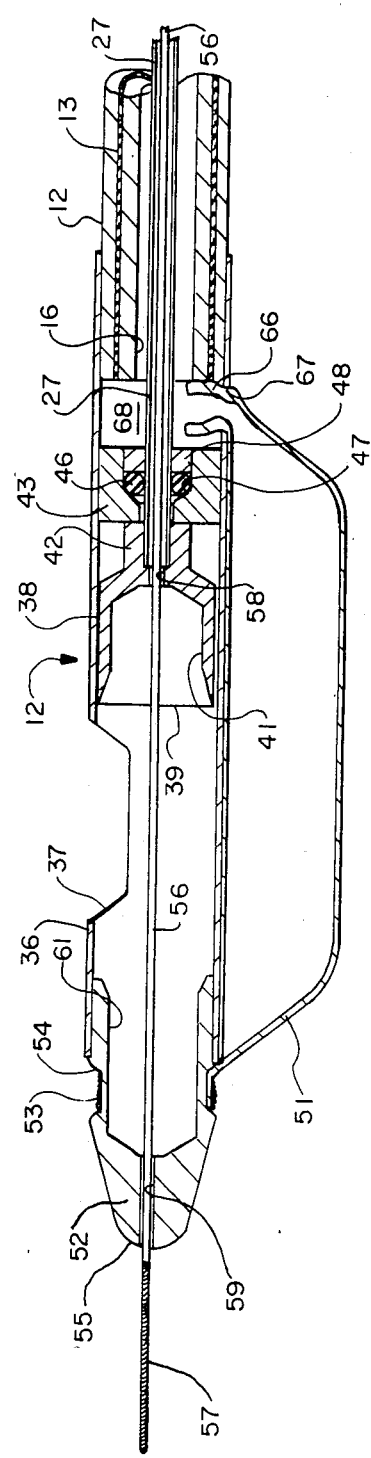
FIG.-1A
FIG.-1B

SINGLE LUMEN ATHERECTOMY CATHETER DEVICE

This invention relates to atherectomy catheter devices and particularly to a single lumen atherectomy catheter device.

In co-pending application Ser. No. 732,691 filed on May 10, 1985, there is disclosed an atherectomy device which utilizes a multi-lumen flexible tubing. One of the lumens can be utilized for the cutter cable whereas another lumen can be utilized as a balloon inflating lumen. Other lumens may be used for introducing radiopaque materials or making pressure measurements and the like. It has been found that the use of such a multi-lumen tubing has certain disadvantages, particularly when it is desired to make a very small catheter apparatus which can be utilized in conjunction with the heart, kidney and the like. By way of example, it is desirable to have tubing which will make possible a five French device and possibly as small a device as a three French device. In addition to having a smaller size, there is the additional desirability of having a tubing which is very flexible. There is therefore a need for a new and improved single lumen atherectomy catheter or a device.

In general, is an object of the present invention to provide an atherectomy catheter which utilizes a single lumen.

Another object of the invention is to provide a device of the above character which can be made very small.

Another object of the invention is to provide a device of the above character which is very flexible.

Another object of the invention is to provide a device of the above character which utilizes a movable guide wire.

Additional objects and features of the invention will appear from the following description in which the preferred embodiments are set forth in detail in conjunction with the accompanying drawings.

FIG. 1A is a view partially in cross section of the proximal end portion of a single lumen catheter incorporating the present invention.

FIG. 1B is an enlarged cross sectional view of the distal end portion of a single lumen catheter incorporating the present invention.

In general the atherectomy device of the present invention is used for removal of material from a atheroma in a vessel of the vascular system of a patient. It is comprised of a generally cylindrical housing having a cutout therein extending longitudinally of the housing on one side of the housing. Atheroma cutting means is disposed within the housing. Flexible guiding means is secured to the proximal end of the housing for advancing the housing into the vessel. Flexible drive means is connected to the atheroma cutting means for operating the atheroma cutting means. Balloon-like inflatable means is carried by the housing and is disposed on the exterior of the housing in a region opposite the side in which the cutout is formed. The flexible guiding means having only a single lumen extending therethrough with the flexible drive means extending through the lumen. Means is coupled to the balloon for establishing communication between the balloon and the single lumen. Fluid-tight means is carried by the housing and the flexible drive means for establishing fluid-tight sealing means between the flexible drive means and the single lumen so that fluid-tight seals are provided between the distal and proximal extremities of the single lumen and the flexible drive means. Means is coupled to the flexible guiding means and in communication with the single lumen in the guiding means for introducing an inflatable medium into the single lumen for inflating the balloon-like member.

More in particular as shown in the drawing, the atherectomy device 11 of the present invention consists of an elongate flexible tubular member 12 formed of suitable plastic material and which can be provided if desired with a braided reinforcement 13. The flexible tubular member 12 can have an outside diameter ranging from 0.050 to 0.200 inches. It is provided with a single or sole lumen 16 extending the length thereof from the proximal to the distal extremities. A fitting 17 is provided near the proximal extremity of the flexible tubular member 12. The fitting 17 serves as a catheter tube attachment. Another fitting 18 is threadedly mounted therein. A rotating seal assembly 19 is mounted in the fitting 18. A single arm adapter 21 is mounted in the rotating seal member 19. As shown in FIG. 1, the proximal extremity of the flexible tubular member 12 extends through the fitting 17 and 18 and through the rotating seal device 19. Thereafter it passes into the proximal extremity of the fitting 21. The side arm 22 of the fitting 21 is in communication with the single or sole passage or lumen 16 in the flexible tubular member 12 and serves as a balloon inflation port.

Another fitting 23 is mounted in the adapter 21. The adapter 21 is provided with a flow passage 24 and the fitting 23 is provided with a flow passage 26. A flexible hollow cutter drive cable 27 is disposed in the passages 24 and 26 in the fittings 21 and 23 and extends into the single lumen 16 provided in the flexible tubular member 12. A fitting 28 having a knurled flange or knob 29 is threaded into the fitting 23 and engages an O-ring 32. The drive cable 27 extends through a passage 33 provided in the fitting 28. The O-ring 32 forms a fluid-tight seal between the fitting 23 and the flexible drive cable 27. The fitting 28 is provided with a tapered portion 28c which is adapted to form a friction fit with a tapered bore 34 in a motor drive unit 35 of the type described in co-pending application Ser. No. 843,743 filed Feb. 28, 1986.

A housing 36 is mounted on the distal extremity of the flexible tubular member 12 and can be formed of a suitable material such as stainless steel. It is generally cylindrical as shown and has its proximal extremity secured to the distal extremity of the flexible tubular member 12 as shown particularly in FIG. 1B. A cutout 37 is provided in the housing 36 in one side thereof and faces in a direction which is generally perpendicular to the longitudinal axis of the housing. A work performing device in the form of a cutter 38 is slidably mounted in the housing 36 and is provided with a circular cutting edge 39 which lies in a plane perpendicular to the longitudinal axis of the housing and the axis of longitudinal movement for the cutter 38. A bell-shaped recess 41 is provided within the cutter 38 and extends rearwardly from the cutting edge 39. The cutter 38 is provided with a hub 42 which is secured to the distal extremity of the flexible drive cable 27.

Means is provided for forming a fluid-tight seal between the housing and the flexible drive cable 27 and consists of a sleeve 43 which is secured within the housing by suitable means such as an adhesive and which is provided with a passage 44 through which the flexible drive cable 27 extends. An O-ring 46 is mounted in a recess 47 and is held in place by a retaining ring 48.

With the construction shown, the O-ring 46 is compressed in such a manner so as form a fluid-tight seal between the sleeve 43 and the flexible drive cable 27.

Means is provided on the exterior of the housing 36 for yieldably urging the housing in the direction the cutout 37 faces and consists of an inflatable balloon 51 which is secured to the housing by suitable means such as an adhesive. The distal extremity of the balloon can be secured in a suitable manner to a nose piece 52 by suitable means such as nylon wire 53 wound into a recess 54 provided in the nose piece 52. The nose piece 52 is secured in the open distal end of the housing 36 by suitable means such as an adhesive. The nose piece 52 is provided with a rounded forwardly extending surface 55.

A conventional flexible elongate guide wire 56 provided with a helical coil spring 57 at its distal extremity is removably mounted in the atherectomy device. The guide wire 56 extends through the hollow flexible drive cable 27, through a bore 58 in the cutter 38, the housing 36 and through a bore 59 provided in the nose piece 52. The guide wire 56 serves as a guiding element for inserting the catheter into a vessel in the vascular system of a patient.

As shown in FIG. 1B, the nose piece 52 is provided with a relatively large recess 61 which opens up into the interior of the housing 36 and extends forwardly from the housing.

The proximal extremity of the balloon 51 is connected in a suitable manner with the single or sole lumen 16 in the flexible tubular member 12 so that the balloon can be inflated and deflated as desired. Thus as shown, the balloon is provided with a reinforced proximal extremity 66 which extends through a hole 67 provided in the housing 27 and opens into a space 68 forward of the sleeve 43 and distal of the distal extremity of the flexible tubular member 12 so that the space 68 is in communication with the single lumen 16.

As described in copending application Ser. No. 843,743, filed Feb. 28, 1986, a thumb flipper member 71 is provided which is secured to the flexible drive cable 27 for moving the flexible drive cable 27 and the cutter 28 carried thereby longitudinally of the axis of rotation of the drive cable 27.

The operation and use of the single lumen atherectomy catheter or device may now be briefly described as follows. In general, the mode of operation of this atherectomy device is very similar to that described in co-pending application Ser. No. 732,691 filed on May 10, 1986. As described in that co-pending application, the atherectomy device 11 can be utilized for removing atheromas or at least portions thereof from a vessel in the vascular system of a patent such as an arterial vessel of the heart. The movable guide wire 56 is inserted into the atherectomy device 11 after the guide wire 56 has been inserted into the vessel of the patient with its distal extremity in the desired position. The proximal extremity of the guide wire 56 is threaded into the nose piece 52, the cutter 38 and into the hollow cutter cable 27. After the device has been inserted into the arterial vessel and is positioned in such a manner so that the cutout 37 is opposite the atheroma, the balloon 51 can be inflated by introducing an inflating medium through the single lumen 16 to urge the housing 36 toward the atheroma so that the atheroma enters the cutout 37. If desired, the guide wire 56 now can be removed and the motor drive unit 35 attached.

With the cutout 37 held in place by the inflated balloon 51, the cutter 38 can be rotated by the motor drive unit 35 to cause rotation of the flexible drive cable 27 and the cutter 38 mounted thereon. The cutter 38 can be advanced by operating the flipper member 71 in a manner described in copending application Ser. No. 843,743 filed Feb. 28, 1986 to advance the cutter to engage the atheroma which has been forced into the cutout 37. The material which is shaved off or removed by the cutter is collected in the recess 41 within the cutter and also can be collected by the recess 61 in the housing 36 as the cutter is advanced beyond the cutout. Thereafter, the atherectomy device can be removed and the material which has been collected within the recesses 41 and 61 are removed. If necessary, the atherectomy device 11 can be inserted repeatedly into the arterial passagee and additional cuts made until as much as desired, or at least a substantial portion of the atheroma has been removed from the vessel so as to permit increased blood flow through the vessel.

From the foregoing it can be seen that the present atherectomy device can be utilized for the same shaving operations on the vessel wall as the atherectomy device disclosed in co-pending application Ser. No. 732,651 filed on May 10, 1985. The construction of the present atherectomy device, however, is much similar because of its use of a single lumen 16 in the flexible tubular member. As can be seen from the construction hereinbefore described, the flexible drive cable 27 for the cutter 38 is disposed in this single lumen 16 which is made possibly by the use of seals provided at the distal and proximal extremities of the flexible drive cable in the form of the O-rings 31 and 46. This construction also makes it possible to utilize the same single lumen 16 for the balloon inflation lumen which can be inflated from the balloon inflation port 22. The balloon 51 is attached to the housing 36 in such a manner so that its proximal extremity opens up directly into the single lumen 16.

In addition with the construction shown, the use of the rotatable member 19 and the rotatable seal provided by the O-ring 46 makes it possible to rotate the housing 27 and the tubular member 12 independent of the motor drive unit 35 and any balloon inflation device connected to the port 22. This facilitates use of the atherectomy device on the operating table when performing the desired operations on the patient.

Also one of the more important features of the present construction for an atherectomy device is that it lends itself to smaller atherectomy devices. Thus an atherectomy device as small as a five French device or even a three French device can be made. The five French device has an outer diameter of less than 0.065, whereas a three French device has an outer diameter of 0.039. By providing atherectomy devices of such a size, it is possible to perform operations in very small blood vessels, as for example, those associated with the heart and kidney, as well as other organs in the body. The construction of the atherectomy device also permits use of a movable guide wire, if desired, in place of a fixed guide wire.

From the foregoing it is apparent that there has been provided an improved atherectomy catheter device which utilizes a single lumen which is particularly useful in connection with making smaller atherectomy devices.

What is claimed is:

1. In an atherectomy device for removal of material from an atheroma in a vessel of the vascular system of a patient, a generally cylindrical housing, said housing being formed with a cutout extending longitudinally of the housing on one side of the housing, atheroma cutting means disposed within the housing, flexible guiding means secured to the proximal end of the housing for advancing the housing into the vessel, flexible drive means connected to the atheroma cutting means for operating the atheroma cutting means, balloon-like inflatable means carried by the housing and disposed on the exterior of the housing opposite the side in which the cutout is formed, said flexible guiding means having only a single lumen extending therethrough, said flexible drive means extending through said single lumen, means coupled to the balloon for establishing communication between the balloon and the single lumen, means including a balloon inflation port coupled to the flexible guiding means and in communication with the single lumen in the guiding means for introducing an inflatable medium into the single lumen for inflating the balloon-like member and fluid-tight means carried by the housing and the flexible guiding means for establishing proximal and distal seals about the flexible drive means so that the single lumen provides a fluid-tight passage between the balloon inflation port and the balloon.

2. A device as in claim 1 together with rotatable coupling means connecting the flexible guiding means to the means forming an inflation port connected into the single lumen so as to permit rotation of the housing and the flexible guiding means independent of rotation of the means providing an inflation port and the flexible drive means.

3. A device as in claim 1 wherein the proximal seal is disposed proximal of the means forming an inflation port.

4. A device as in claim 1 wherein said distal sealing means is disposed distal of the distal extremity of the single lumen.

5. A device as in claim 1 wherein said distal sealing means is disposed within the housing.

6. A device as in claim 1 together with a movable guide wire carried by the same.

7. A device as in claim 6 wherein the movable guide wire extends through the flexible drive means.

* * * * *